(12) United States Patent
Wang et al.

(10) Patent No.: US 10,485,735 B2
(45) Date of Patent: Nov. 26, 2019

(54) COMPOSITIONS AND METHODS FOR BIOACTIVE DENTAL COMPOSITES

(71) Applicants: Tongxin Wang, Berwyn Heights, MD (US); Lawrence C. Chow, Germantown, MD (US)

(72) Inventors: Tongxin Wang, Berwyn Heights, MD (US); Lawrence C. Chow, Germantown, MD (US)

(73) Assignee: HOWARD UNIVERSITY, Washington, DC (US)

( * ) Notice: Subject to any disclaimer, the term of this patent is extended or adjusted under 35 U.S.C. 154(b) by 0 days.

(21) Appl. No.: 14/895,771

(22) PCT Filed: Jun. 6, 2014

(86) PCT No.: PCT/US2014/041306
§ 371 (c)(1),
(2) Date: Dec. 3, 2015

(87) PCT Pub. No.: WO2014/197797
PCT Pub. Date: Dec. 11, 2014

(65) Prior Publication Data
US 2016/0113844 A1    Apr. 28, 2016

Related U.S. Application Data

(60) Provisional application No. 61/832,366, filed on Jun. 7, 2013.

(51) Int. Cl.
*A61K 6/00* (2006.01)
*A61K 6/083* (2006.01)

(52) U.S. Cl.
CPC ............ *A61K 6/0085* (2013.01); *A61K 6/083* (2013.01)

(58) Field of Classification Search
None
See application file for complete search history.

(56) References Cited

U.S. PATENT DOCUMENTS

| | | | |
|---|---|---|---|
| 6,444,724 B1 * | 9/2002 | Stangel | A61K 6/0073 523/115 |
| 6,953,832 B2 | 10/2005 | Moszner et al. | |
| 2007/0238803 A1 * | 10/2007 | Bissinger | A61K 6/083 522/77 |
| 2007/0269768 A1 | 11/2007 | Rusin et al. | |

(Continued)

FOREIGN PATENT DOCUMENTS

EP    2 444 054 A1    4/2012

OTHER PUBLICATIONS

European Patent Office, Extended European Search Report dated Feb. 22, 2017 for European Patent Application No. 14807448.7 (6 pages).

(Continued)

*Primary Examiner* — Bethany P Barham
*Assistant Examiner* — Dominic Lazaro
(74) *Attorney, Agent, or Firm* — Sughrue Mion, PLLC

(57) ABSTRACT

Described herein are compositions and methods which produce hydrolytically stable resin monomers, bioactive fillers, phosphorus coupling agent and surface coating method, which can be combined to produce new generation dental composites; compositions comprising the same, as well as methods of making and using the same are also described.

15 Claims, 11 Drawing Sheets

(56) References Cited

U.S. PATENT DOCUMENTS

2008/0070193 A1 3/2008 Bissinger et al.
2009/0270527 A1 10/2009 Lin et al.
2011/0045436 A1* 2/2011 Rusin ................. A61C 13/0022
433/173

OTHER PUBLICATIONS

PCT International Search Report and Written Opinion of the International Searching Authority dated Sep. 30, 2014 for International Application No. PCT/US2014/041306 (15 pages).
Ulrich Salz and Thorsten Bock, Adhesion Performance of New Hydrolytically Stable One-component Self-etching Enamel/Dentin Adhesives, The Journal of Adhesive Dentistry, 2010, vol. 12, No. 1, pp. 7-10.
Kunio Ikemura and Takeshi Endo, A review of our development of dental adhesives—Effects of radical polymerization initiators and adhesive monomers on adhesion, Dental Materials Journal, 2010, vol. 29, No. 2, pp. 109-121.

* cited by examiner

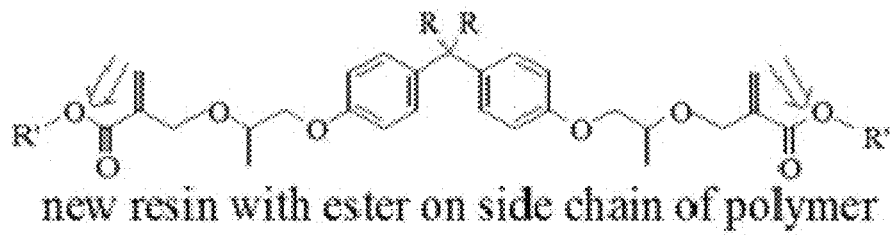

new resin with ester on side chain of polymer

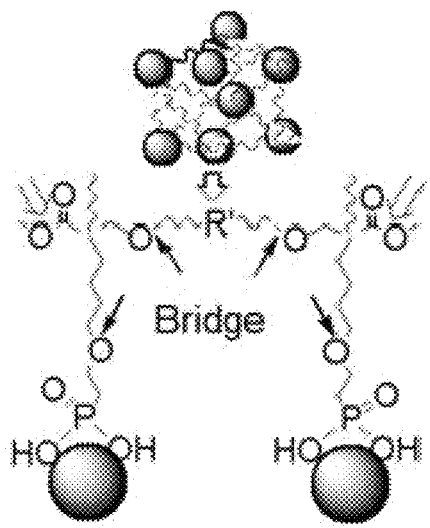

⇒ Hydrolysis of the arrow ⇒indicated ester bonds will not affect the cross-linked polymeric matrix and the interface between matrix and filler.

→ Arrow →indicated ether bonds within main backbone of polymeric backbone will not hydrolyze, so the matrix and the interfacial adhesion will not be affected by aqueous aging.

*Fig. 2*

Fig. 8: NMR spectra of ester-B (5a) in CDCl₃.

Fig 11: NMR spectra of ether-C (6) in CDCl₃.

COMPOSITIONS AND METHODS FOR BIOACTIVE DENTAL COMPOSITES

CROSS-REFERENCE TO RELATED APPLICATIONS

This application is a U.S. national phase application filed under 35 U.S.C. § 371 of International Application Number PCT/US2014/041306, filed Jun. 6, 2014, designating the United States, which claims benefit of U.S. Provisional Application No. 61/832,366, filed Jun. 7, 2013, which are hereby incorporated herein by reference in their entirety.

FIELD

This application is directed to the compositions and methods to produce dental composites with less degradation, prolonged lifespan and improved bioactivity.

BACKGROUND

Tooth-colored resin composites are being widely used for direct restoration of teeth. (Moszner, N., Hirt, T., "New Polymer-Chemical Developments in Clinical Dental Polymer Materials: Enamel-Dentin Adhesives and Restorative Composites," *Journal of Polymer Science Part A: Polymer Chemistry*, 2012, 50(21), 4369-4402; Moszner, N., Salz, U., "Recent Developments of New Components for Dental Adhesives and Composites," *Macromolecular Materials and Engineering*, 2007, 292: 245-271.) "The increasing use of dental composites restorative systems and the associated dentin/enamel bonding agents is approaching approximately 65-70% of dental restorations placed in USA," (2012 NIH/NIDCR Funding Opportunity Announcement: Design and Development of Novel Dental Composite Restorative Systems (U01), RFA-DE-13-001, Sep. 12, 2012; American Dental Association (ADA), "The 1999 Survey of Dental Services Rendered," Chicago, Ill., ADA Survey Center, 2002.) However, recent reports show that half of current dental restorations fail within 10 years. (Frost, P. M., "An Audit on The Placement and Replacement of Restorations in a General Dental Practice," *Primary Dental Care*, 2002, 9: 31-36; National Institute of Dental and Craniofacial Research (NIDCR) Announcement No. 13-DE-102, Dental Resin Composites and Caries, Mar. 5, 2009.) The replacement of the failed restorations accounts for about 50-70% of all restorations work (ca $5 billion/year cost) in the USA. (Jokstad, A., Bayne, S., Blunck, U. Tyas, M., Wilson, N., "Quality of Dental Restorations. FDI Commission Projects 2-95," *International Dental Journal*, 2001, 51: 117-158; Deligeorgi, V., Mjor, I. A., Wilson, N. H., "An Overview of Reasons for the Placement and Replacement of Restorations," *Primary Dental Care*, 2001, 8: 5-11.)

One critical problem of the current composites is the balk fracture due to their degradation of the polymeric matrix and/or interface in oral environment (Soncini, J. A., Maserejian, N. M., Trachtenberg, G. H., Tavares, M., Hayes, C., "The Longevity of Amalgam Versus Compomer/Composite Restorations in Posterior Primary and Permanent Teeth," *Journal of the American Dental Association*, 2007, 138: 763-772; Bernardo, M. Luis, H., Martin, M. D., Leroux, B. G., Rue, T., Leitão, J., DeRouen, T. A., "Survival and Reasons for Failure of Amalgam Versus Composite Posterior Restorations Placed in a Randomized Clinical Trial," *Journal of the American Dental Association*, 2007, 138: 775-783), leading to early failure and short lifespan (Ferracane, J. L., Hopkin, J. K., Condon, J. R., "Properties of Heat-Treated Composites After Aging in Water," *Dental Materials*, 1995, 11: 354-358; Ferracane, J. L., "Current Trends in Dental Composites," *Critical Reviews in Oral Biology & Medicine*, 1995, 6: 302-318), and release of potential toxic compounds from composites. (Gonçalves, T. S., Morganti, M. A., Campos, L. C., Rizzatto, S. M., Menezes, L. M., "Allergy to Auto-Polymerized Acrylic Resin in an Orthodontic Patient." *American Journal of Orthodontics and Dentofacial Orthopedics*, 2006, 129: 431-435.) Therefore, it is imperative to develop new composite system, which is hydrolytically stable, thus they can avoid early failure, prolong clinical service lifespan, and save the replacement cost.

Currently used dental composites include an initiator and three major components: polymeric matrix, glass filler, and silane coupling agent. Since introduced by Bowen in the early 1960s (Bowen, R. L., "Dental Filling Material Comprising Vinyl-Silane Treated Fused Silica and a Binder Consisting of the Reaction Product of Bisphenol and Glycidyl Methacrylate," U.S. Pat. No. 3,066,112, 1962; Bowen, R. L., "Properties of a Silica-Reinforced Polymer for Dental Restoration," *Journal of the American Dental Association*, 1963, 66: 57-64), the resin chemistry for current composites on the market has not changed: bisphenol-A-diglycidyl dimethacrylate (BisGMA), urethane dimethacrylate (UDMA) and Methylene glycol dimethacrylate (TEGDMA). (O'Brien, W. J., *Dental Materials and Their Selection*, Edition 3, Quintessence Publishing Company, Inc., Polymeric Restorative Materials, 2002; 113-131; Gladwin, M., Bagby, M., *Clinical Aspects of Dental Materials: Theory, Practice, and Cases*, 3rd Edition, Lippincott, Williams & Wilkins, Baltimore, 2009.)

During clinical application, these monomers and coupling agent (e.g., 3-methacryloxypropyltrimethyoxy silane, MPS) on the surface of the filler will form a cross-linked polymeric matrix, in which the ester bonds plays the roles as "bridge" within the polymeric matrix and the interface between matrix and filler (FIG. 1).

However, these "bridge" ester bonds may degrade in the oral cavity, which can be accelerated by acid (such as bacteria acid and soft drinks), or salivary enzymes. (Santerre, J. P., Shajii, L., Leung, B. W., "Relation of Dental Composite Formulations to Their Degradation and the Release of Hydrolyzed Polymeric-Resin-Derived Products, *Critical Reviews in Oral Biology & Medicine*, 2001, 12: 136-151.) Hydrolysis of these "bridge" esters will breakdown the polymer backbone and the interface, thus reducing the mechanical strength (FIG. 1). (Finer Y., Santerre, J. P., "Salivary Esterase Activity and its Association with the Biodegradation of Dental Composites," *Journal of Dental Research*, 2004, 83: 22-26; Yourtee, D. M., Smith, R. E., Russo, K. A., Burmaster, S, Cannon, J. M., Eick, J. D., Kostoryz, E. L., "The Stability of Methacrylate Biomaterials When Enzyme Challenged: Kinetic and Systematic Evaluations," *Journal of Biomedical Materials Research*, 2001, 57: 522-531.)

SUMMARY

Therefore, new composites including new hydrolytically stable monomer/polymer matrix, new coupling agent and new filler have been developed.

In one form, there is no ester or amide bond on the main backbone, so that their hydrolysis will not break down the polymeric matrix and interface.

According to one form, there is no hydrolysable bond, such as an ester or amide bond, between the polymerizable double bond, thus their hydrolysis will not break down the polymeric matrix and interface.

In one form, the monomer and polymer matrix may replace the ester bonds by less hydrolysable groups or non-hydrolysable groups.

In one form, the less hydrolysable group can be an amide (or other less hydrolysable bond).

In one form, the composition includes:

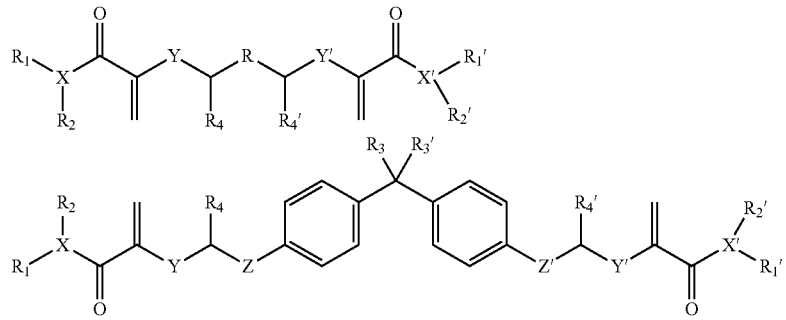

where R is selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$ or any combination thereof, where p and q are independently=0, 1, 2, 3, 4, 5, 6, 7, 8, 9, 10, 11, 12, 13, 14, 15, 16, 17, 18, 19, or 20;

where X, Y, Z, X', Y', and/or Z' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$ or any combination thereof, where p, q, m are independently=0, 1, 2, 3, 4, 5, 6, 7, 8, 9, 10, 11, 12, 13, 14, 15, 16, 17, 18, 19, or 20;

where R1, R1', R2, and/or R2' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$, —COOH, —$PO_3H_2$ or any combination thereof, where p, q, m are independently=0, 1, 2, 3, 4, 5, 6, 7, 8, 9, 10, 11, 12, 13, 14, 15, 16, 17, 18, 19, or 20;

where R3, R4, R3', and/or R4' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$, —COOH, —$PO_3H_2$ or any combination thereof, where p, q, m are independently=0, 1, 2, 3, 4, 5, 6, 7, 8, 9, 10, 11, 12, 13, 14, 15, 16, 17, 18, 19, or 20.

In one form, the composition includes:

where R is selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$ or any combination thereof, where p, q are independently=0, 1, 2, 3, 4, 5, 6, 7, 8, 9, 10, 11, 12, 13, 14, 15, 16, 17, 18, 19, or 20;

where Y, Z, Y' and/or Z' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$ or any combination thereof, or combination with any of —OH, —COOH, —$PO_3H_2$, where p, q, m are independently=0, 1, 2, 3, 4, 5, 6, 7, 8, 9, 10, 11, 12, 13, 14, 15, 16, 17, 18, 19, or 20;

where R1, R1', R2, and/or R2' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$, —COOH, —$PO_3H_2$ or any combination thereof, where p, q, m are independently=0, 1, 2, 3, 4, 5, 6, 7, 8, 9, 10, 11, 12, 13, 14, 15, 16, 17, 18, 19, or 20;

where R3, R4, R3', and/or R4' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$, —COOH, —$PO_3H_2$ or any combination thereof, where p, q, m are independently=0, 1, 2, 3, 4, 5, 6, 7, 8, 9, 10, 11, 12, 13, 14, 15, 16, 17, 18, 19, or 20.

In one form, the less hydrolysable group may be a non-hydrolysable ether or sulfide or nitrogen containing chain or alkyl chain. According to one form, the composition includes:

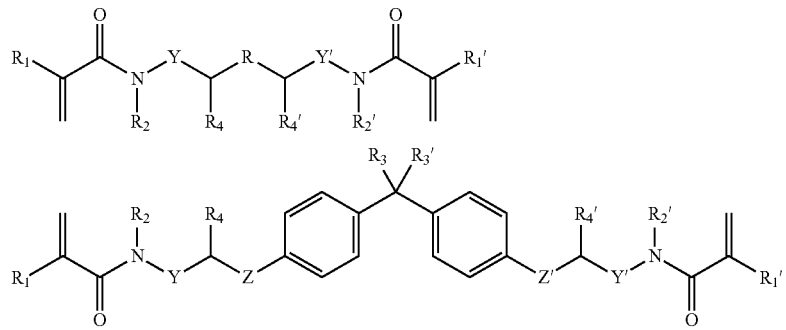

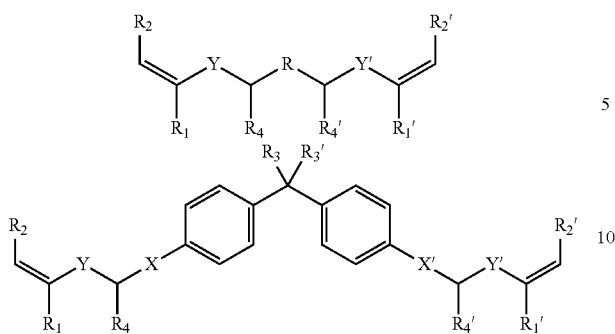

where R is selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$ or any combination thereof, where p, q are independently=0, 1, 2, 3, 4, 5, 6, 7, 8, 9, 10, 11, 12, 13, 14, 15, 16, 17, 18, 19, or 20;

where X, Y, X' and/or Y' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$ or any combination thereof, where p, q, m are independently=0, 1, 2, 3, 4, 5, 6, 7, 8, 9, 10, 11, 12, 13, 14, 15, 16, 17, 18, 19, or 20;

where R1, R1', R2, and/or R2' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$, —COOH, —$PO_3H_2$ or any combination thereof, where p, q, m are independently=0, 1, 2, 3, 4, 5, 6, 7, 8, 9, 10, 11, 12, 13, 14, 15, 16, 17, 18, 19, or 20;

where R3, R4, R3', and/or R4' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$, —COOH, —$PO_3H_2$ or any combination thereof, where p, q, m are independently=0, 1, 2, 3, 4, 5, 6, 7, 8, 9, 10, 11, 12, 13, 14, 15, 16, 17, 18, 19, or 20.

In another form, there is no ester or amide bonds on the main backbone, thus their hydrolysis will not breakdown the polymeric matrix and interface (FIG. 2).

In one form, one or more highly dense ceramic fluorapatite (FA) fillers are used as the filler to fabricate the composites. In another form, the filler is a partially fluoridated hydroxyapatite (FHA) comprising $Ca_{10}(PO_4)_6F_x(OH)_{(1-x)}$, where x=from 0 to 1. In another form the filler is ceramically prepared particles comprising homogeneous mixture of fluoridated hydroxyapatite and calcium fluoride. In another form, other calcium phosphate filler such as ACP (amorphous calcium phosphate), TCP (tricalcium phosphate), DCP (dicalcium phosphate), MCP (monocalcium phosphate) or HA (hydroxyapatite) and mixtures thereof can be used as the filler. Due to the similar composition to teeth, the bioactive FA filler is more likely to induce mineralization than bioinert quartz filler, thus forming an excellent interface to eliminate the marginal leakage.

In addition to the above bioactive filler, the composite can also include any other bioactive/bioinert filler including bioglass, quartz, glass, silicate, Ba/Sr/silicate glass, metal oxides ($ZrO_2$, $TiO_2$, $Al_2O_3$), $YbF_3$, and the like.

In one form, a new coupling agent (phosphorus containing coupling agent such as phosphoric or phosphorylate coupling gent) other than conventionally used silane coupling agents may be used for the calcium phosphate filler. The phosphonic group can bind with FA filler and composite and tooth and attract and increase $Ca^{2+}$ micro-concentration, thus promoting the mineralization. In another form, carboxylate coupling agent can be also applied to calcium phosphate or FA filler.

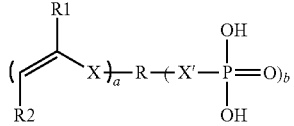

where R, R1 and/or R2 are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$ or any combination thereof, where p, q are independently=0, 1, 2, 3, 4, 5, 6, 7, 8, 9, 10, 11, 12, 13, 14, 15, 16, 17, 18, 19, or 20;

where X, and/or X' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$;

where the number of a, or b can independently be 1, 2, 3, 4, 5, 6, 7, 8, 9, and/or 10;

where the phosphorus group can be replaced by carboxylic, sulfonic, hydroxyl or amine group.

BRIEF DESCRIPTION OF THE DRAWINGS

FIG. 2 illustrates one scheme showing less impact to the polymer backbone and mechanical strength from the degradation of the newly developed resins, which have high resistance to hydrolysis, because no ester bonds are within the main polymer backbone;

DETAILED DESCRIPTION

Figure 1:
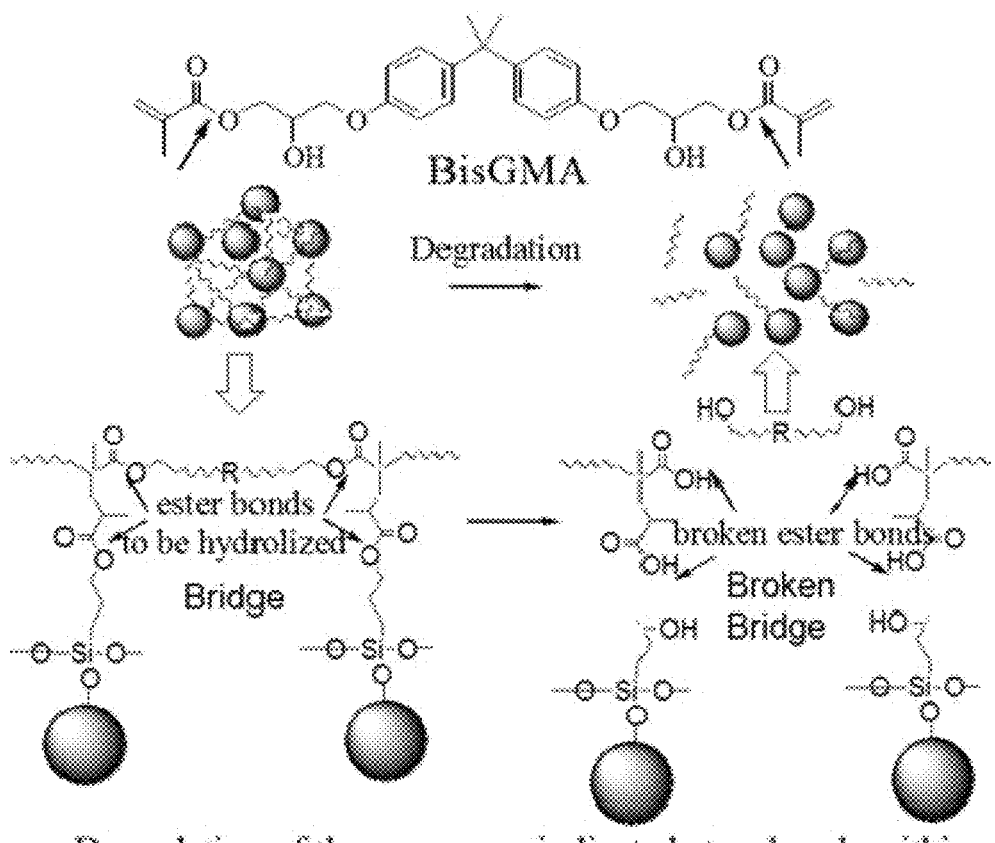
FIG. 1 illustrates one scheme for the degradation of conventional resin and coupling agent resulting from the hydrolysis of the ester bonds. Such degradation leads to breakdown of polymer matrix and reduced mechanical strength.
Figure 3:
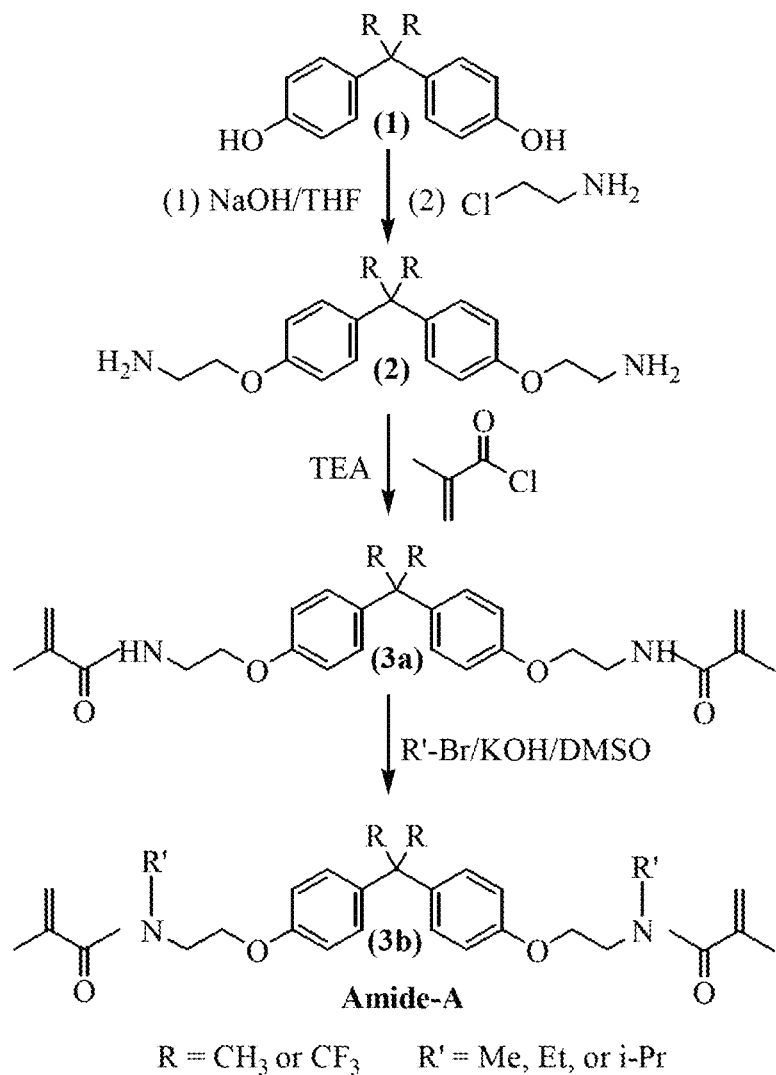
FIG. 3 illustrates one scheme showing the synthesis of the monomer containing amide group.
Figure 4:
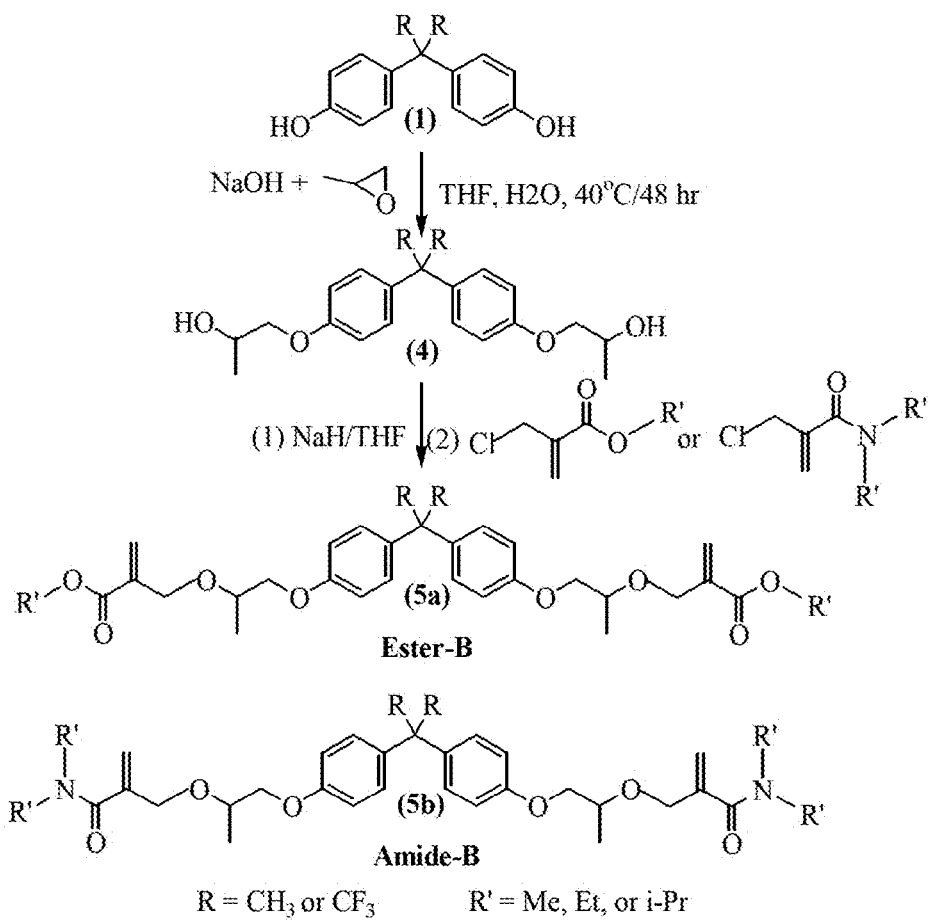
FIG. 4 illustrates one scheme showing the synthesis of monomers with an ester or amide on a side chain of the polymeric matrix.

A variety of compositions may be prepared as described herein. For example a variety of exemplary syntheses are provided in FIGS. 3-7. Further exemplary materials are illustrated in FIG. 2 as well as shown in the resulting compositions in FIGS. 3-7.

The monomers described herein may be used in a variety of applications, such as dental applications. For example, in one form, the monomer may be used to form a polymeric matrix for use in a dental composition. In another form, the monomer may be provided in a polymeric matrix along with bioactive filler, a coupling agent and an optional surface coating.

In one form, the composition includes:

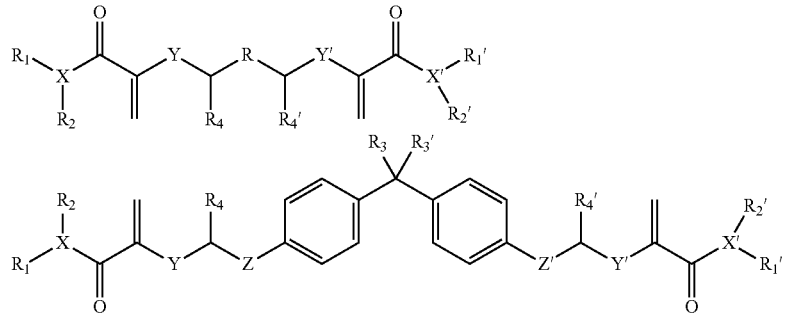

where R is selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$ or any combination thereof, where p and q are independently=0, 1, 2, 3, 4, 5, 6, 7, 8, 9, 10, 11, 12, 13, 14, 15, 16, 17, 18, 19, or 20;

where X, Y, Z, X', Y', and/or Z' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$ or any combination thereof, where p, q, m are independently=0, 1, 2, 3, 4, 5, 6, 7, 8, 9, 10, 11, 12, 13, 14, 15, 16, 17, 18, 19, or 20;

where R1, R1', R2, and/or R2' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$, —COOH, —$PO_3H_2$ or any combination thereof, where p, q, m are independently=0, 1, 2, 3, 4, 5, 6, 7, 8, 9, 10, 11, 12, 13, 14, 15, 16, 17, 18, 19, or 20;

where R3, R4, R3', and/or R4' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$, —COOH, —$PO_3H_2$ or any combination thereof, where p, q, m are independently=0, 1, 2, 3, 4, 5, 6, 7, 8, 9, 10, 11, 12, 13, 14, 15, 16, 17, 18, 19, or 20.

In one form, the composition includes:

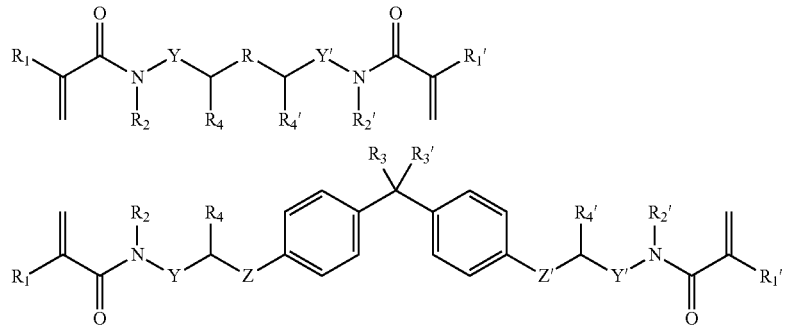

where R is selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$ or any combination thereof, where p, q are independently=0, 1, 2, 3, 4, 5, 6, 7, 8, 9, 10, 11, 12, 13, 14, 15, 16, 17, 18, 19, or 20;

where Y, Z, Y' and/or Z' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$ or any combination thereof, or combination with any of —OH, —COOH, —$PO_3H_2$, where p, q, m are independently=0, 1, 2, 3, 4, 5, 6, 7, 8, 9, 10, 11, 12, 13, 14, 15, 16, 17, 18, 19, or 20;

where R1, R1', R2, and/or R2' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$, —COOH, —$PO_3H_2$ or any combination thereof, where p, q, m are independently=0, 1, 2, 3, 4, 5, 6, 7, 8, 9, 10, 11, 12, 13, 14, 15, 16, 17, 18, 19, or 20;

where R3, R4, R3', and/or R4' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$, —COOH, —$PO_3H_2$ or any combination thereof, where p, q, m are independently=0, 1, 2, 3, 4, 5, 6, 7, 8, 9, 10, 11, 12, 13, 14, 15, 16, 17, 18, 19, or 20.

According to one form, the composition includes:

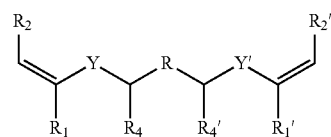

-continued

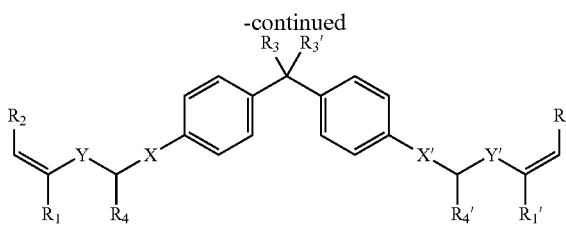

where R is selected from the group consisting of: B, C, Si, O, S, N, P, H, $(CH_2)_p$, $(CF_2)_q$, $(CHF)_q$, C=O, C=C, C≡C, benzyl, phenyl, F, Cl, Br, I, $NO_2$ or any combination thereof, where p, q are independently=0, 1, 2, 3, 4, 5, 6, 7, 8, 9, 10, 11, 12, 13, 14, 15, 16, 17, 18, 19, or 20;

where X, Y, X' and/or Y' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$ or any combination thereof, where p, q, m are independently=0, 1, 2, 3, 4, 5, 6, 7, 8, 9, 10, 11, 12, 13, 14, 15, 16, 17, 18, 19, or 20;

where R1, R1', R2, and/or R2' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$, —COOH, —$PO_3H_2$ or any combination thereof, where p, q, m are independently=0, 1, 2, 3, 4, 5, 6, 7, 8, 9, 10, 11, 12, 13, 14, 15, 16, 17, 18, 19, or 20;

where R3, R4, R3', and/or R4' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$, —COOH, —$PO_3H_2$ or any combination thereof, where p, q, m are independently=0, 1, 2, 3, 4, 5, 6, 7, 8, 9, 10, 11, 12, 13, 14, 15, 16, 17, 18, 19, or 20.

According to one form, the monomer has the structure of formula 3b, which is prepared from less hydrolysable amide:

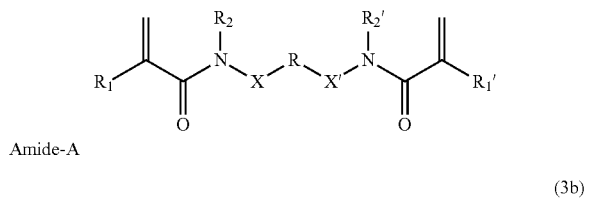

Amide-A (3b)

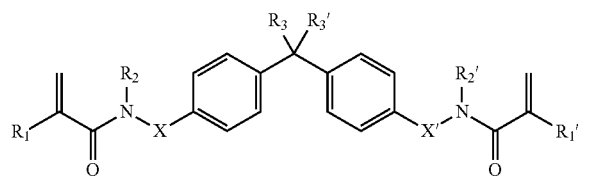

where R is selected from the group consisting of O, S, N, H, $(CH_2)_p$, $(CF_2)_q$, or any combination thereof, where p, q can each independently be=0, 1, 2, 3, 4, 5, 6, 7, 8, 9, 10, 11, 12, 13, 14, 15, 16, 17, 18, 19, or 20;

where R1, and/or R1' are each independently selected from the group consisting of H, $(CH_2)_p$, $(CF_2)_q$, $(CH_2CH_2O)_m$ or any combination thereof, where p, q, m can each independently be=0, 1, 2, 3, 4, 5, 6, 7, 8, 9, or 10;

where R2, and/or R2' are each independently selected from the group consisting of H, $(CH_2)_p$, $(CF_2)_q$, $(CH_2CH_2O)_m$ or any combination thereof, where p, q, m can each independently be=0, 1, 2, 3, 4, 5, 6, 7, 8, 9, or 10;

where R3, and/or R3' are each independently selected from the group consisting of H, $(CH_2)_p$, $(CF_2)_q$, $(CH_2CH_2O)_m$ or any combination thereof, where p, q, m can each independently be=0, 1, 2, 3, 4, 5, 6, 7, 8, 9, or 10;

where X, and/or X' are each independently selected from the group consisting of O, S, N, H, $(CH_2)_p$, $(CF_2)_q$, $(CH_2O)_m$, or any combination thereof, or combination with any of —OH, —COOH, —$PO_3H_2$, where p, q, m can each independently be=0, 1, 2, 3, 4, 5, 6, 7, 8, 9, 10, 11, 12, 13, 14, 15, 16, 17, 18, 19, or 20.

In yet another form, one type of the monomer has the structure of formula 6, which is prepared from non-hydrolysable ether:

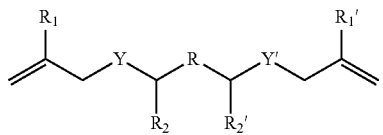

Ether-C (6)

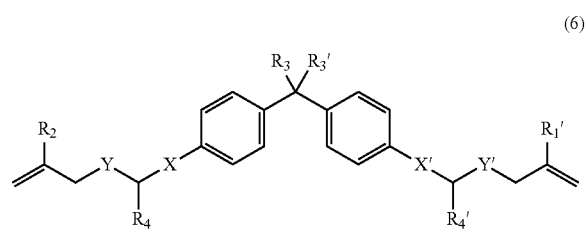

where R is selected from the group consisting of O, S, N, H, $(CH_2)_p$, $(CF_2)_q$, or any combination thereof, where p, q can each independently be=0, 1, 2, 3, 4, 5, 6, 7, 8, 9, 10, 11, 12, 13, 14, 15, 16, 17, 18, 19, or 20;

where X, and/or X' are each independently selected from the group consisting of O, S, N, H, $(CH_2)_p$, $(CF_2)_q$, $(CH_2CH_2O)_m$ or any combination thereof, where p, q, m can each independently be=0, 1, 2, 3, 4, 5, 6, 7, 8, 9, 10, 11, 12, 13, 14, 15, 16, 17, 18, 19, or 20;

where Y, and/or Y' are each independently selected from the group consisting of O, S, N, H, $(CH_2)_p$, $(CF_2)_q$, $(CH_2CH_2O)_m$ or any combination thereof, where p, q, m can each independently be=0, 1, 2, 3, 4, 5, 6, 7, 8, 9, 10, 11, 12, 13, 14, 15, 16, 17, 18, 19, or 20;

where R1, and/or R1' are each independently selected from the group consisting of H, $(CH_2)_p$, $(CF_2)_q$, $CH_2CH_2O)_m$ or any combination thereof, where p, q, m can each independently be=0, 1, 2, 3, 4, 5, 6, 7, 8, 9, or 10;

where R2, and/or R2' are each independently selected from the group consisting of H, OH, —COOH, —$PO_3H_2$, $(CH_2)_p$, $(CF_2)_q$, $(CH_2CH_2O)_m$ or any combination thereof, where p, q, m can each independently be=0, 1, 2, 3, 4, 5, 6, 7, 8, 9, or 10;

where R3, and/or R3' are each independently selected from the group consisting of H, $(CH_2)_p$, $(CF_2)_q$, $(CH_2CH_2O)_m$ or any combination thereof, where p, q, m can each independently be=0, 1, 2, 3, 4, 5, 6, 7, 8, 9, or 10.

In yet another form, one type of the monomer has the structure of formula 5b, wherein the ester or amide moieties are NOT within polymer backbone:

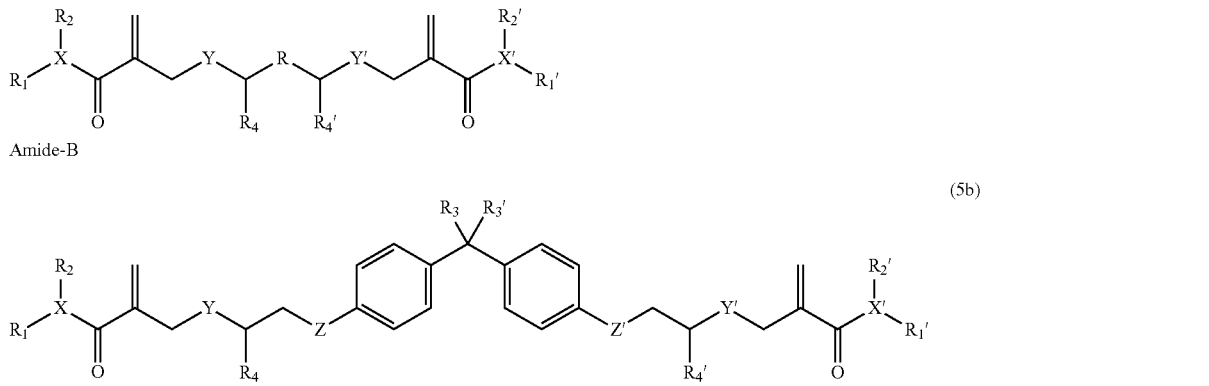

Amide-B (5b)

where R is selected from the group consisting of O, S, N, H, $(CH_2)_p$, $(CF_2)_q$, or any combination thereof, where p, q can each independently be=0, 1, 2, 3, 4, 5, 6, 7, 8, 9, 10, 11, 12, 13, 14, 15, 16, 17, 18, 19, or 20;

where X, and/or X' are each independently selected from the group consisting of O, or N;

where Y, Z, Y', and/or Z' are each independently selected from the group consisting of O, S, N, H, $(CH_2)_p$, $(CF_2)_q$, $(CH_2CH_2O)_m$ or any combination thereof, where p, q, m can each independently be=0, 1, 2, 3, 4, 5, 6, 7, 8, 9, 10, 11, 12, 13, 14, 15, 16, 17, 18, 19, or 20;

where R1, R1', R2, and/or R2' are each independently selected from the group consisting of H, $(CH_2)_p$, $(CF_2)_q$, $(CH_2CH_2O)_m$ or any combination thereof, where p, q, m can each independently be=0, 1, 2, 3, 4, 5, 6, 7, 8, 9, or 10;

where R4, and/or R4' are each independently selected from the group consisting of H, OH, —COOH, —PO3H2, $(CH_2)_p$, $(CF_2)_q$, $(CH_2CH_2O)_m$ or any combination thereof, where p, q, m can each independently be=0, 1, 2, 3, 4, 5, 6, 7, 8, 9, or 10;

where R3, and/or R3' are each independently selected from the group consisting of H, $(CH_2)_p$, $(CF_2)_q$, $(CH_2CH_2O)_m$ or any combination thereof, where p, q, m can each independently be=0, 1, 2, 3, 4, 5, 6, 7, 8, 9, or 10.

It should be noted that the monomer can have calcium binding group selected from the group consisting of: phosphonic, phosphoryl, carboxylic, sulfonic, hydroxyl, amino, as well as their ester or salt (sodium, potassium, ammonium) and combination or mixtures thereof.

In one form, the monomers of resin comprise the new resin monomers having greater water resistance than currently used BisGMA and TEGDMA.

It should be understood that the synthetic pathways to form the resins of the preceding claims can be different reactions including coupling, click, addition, substitution, condensation, esterification, and amide reaction.

According to one form, the bioactive filler may include at least one material selected from the group consisting of: FA (fluorapatite), HA (hydroapatite), FHA (fluorhydroxyapatite), ACP (amorphous calcium phosphate), TCP (tricalcium phosphate), TTCP (tetracalcium phosphate), DCP (dicalcium phosphate), MCP (monocalcium phosphate), bioglass, quartz, glass, silicate, Ba/Sr/silicate glass, metal oxides $(ZrO_2, TiO_2, Al_2O_3)$, $YbF_3$, and combinations thereof.

In addition to the above bioactive fillers, additional filler such as bioglass, quartz, glass, silicate, Ba/Sr/silicate glass, metal oxides $(ZrO_2, TiO_2, Al_2O_3)$, $YbF_3$, and combinations thereof can be included.

In one form, the coupling agent may include FA or calcium phosphate binding groups, comprising phosphorus binding groups selected from the group consisting of: phosphonic acid group (R—PO3H2), phosphoryl acid group (—O—PO3H2), as well as their ester or salt (e.g., sodium or potassium, ammonium), and combinations and mixtures thereof. According to one form, the coupling agent includes a material selected from the group consisting of: phosphorus group, carboxylic acid group, hydroxyl group, amino group, sulfonic acid group, as well as their ester or salt (e.g., sodium or potassium, ammonium), and combination and mixtures thereof.

For example, the coupling agent may have the general formula:

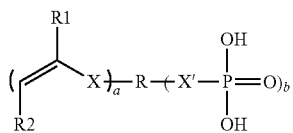

where R, R1 and/or R2 are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$ or any combination thereof, where p, q are independently=0, 1, 2, 3, 4, 5, 6, 7, 8, 9, 10, 11, 12, 13, 14, 15, 16, 17, 18, 19, or 20;

where X, and/or X' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$;

where the number of a, or b can each independently be 1, 2, 3, 4, 5, 6, 7, 8, 9, and/or 10;

where the phosphorus group can be replaced by carboxylic, sulfonic, hydroxyl or amine group.

In another form, the coupling agent may have the general formula:

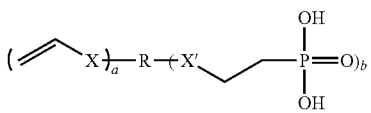

where R is selected from the group consisting of O, S, N, H, $(CH_2)_p$, $(CF_2)_q$, or any combination thereof, where p, q are independently=0, 1, 2, 3, 4, 5, 6, 7, 8, 9, 10, 11, 12, 13, 14, 15, 16, 17, 18, 19, or 20;

where X, or X' are independently selected from the group consisting of CH2, O, S, or N;

where the number of a, or b can independently be 1, 2, 3, 4, 5, 6, 7, 8, 9, 10;

where the phosphorus group can be replaced by carboxylic, sulfonic, hydroxyl or amine groups;

wherein it has number of phosphonic group and C=C double bonds can be 1, 2, 3, 4, 5, 6, 7, 8, 9, 10.

According to one form, the surface coatings may include silane coupling agent, isocyanates coupling agent, titanate coupling agent, zirconate coupling agent, and the like.

In one form, the filler can be coated after preparation of the filler or by combining surface coating and ball milling in a single step

EXAMPLES AND TESTS

1. Synthesis hydrolytically stable monomers
2. Synthesis FA filler
3. Synthesis coupling agent
4. Fabricate composites A number of strategies are contemplated for forming less hydrolysable resins. Strategy#1: synthesize monomers in which esters are replaced by amides. See, for example FIG. 3. Amide's hydrolysis half-life is 38,000 fold of ester. Recent studies on some amide resins for adhesive application confirmed the hydrolytic stability. Therefore, the amide resin has less mechanical reduction in the oral cavity than BisGMA.

Strategy#2: synthesize monomers in which hydrolysable ester or amide bonds will be moved to the polymer side chain. Because hydrolysis of side chain does not breakdown the polymeric matrix (FIG. 4) this polymer has greater mechanical strength than n BisGMA after aging in the oral cavity.

Figure 5:
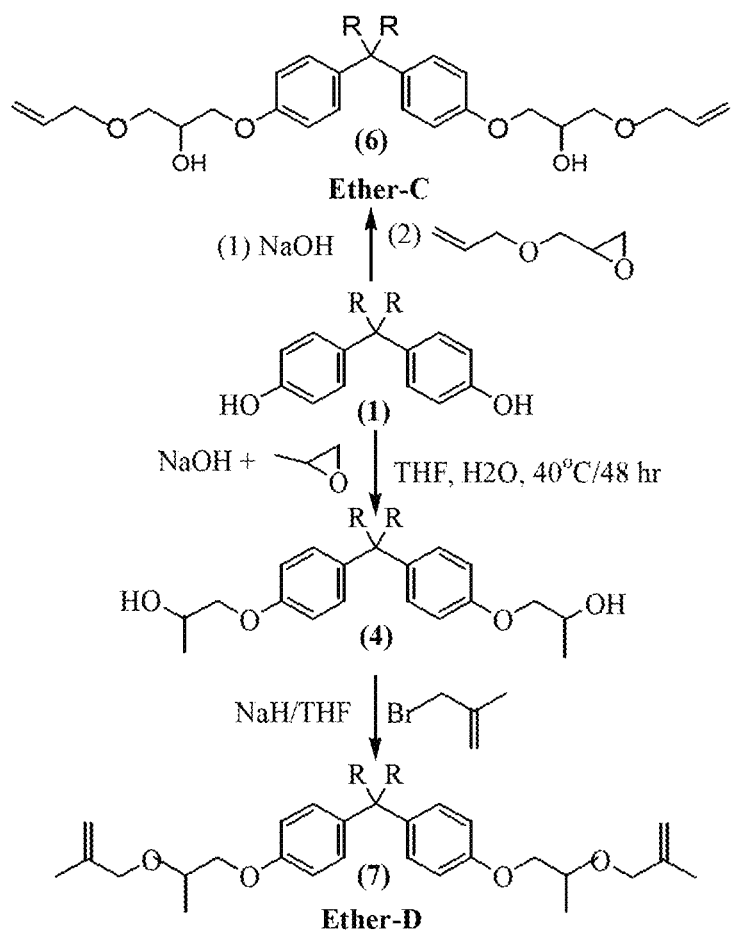
FIG. 5 illustrates one scheme of the synthesis of monomers with non-hydrolysable ether.
Figure 6:
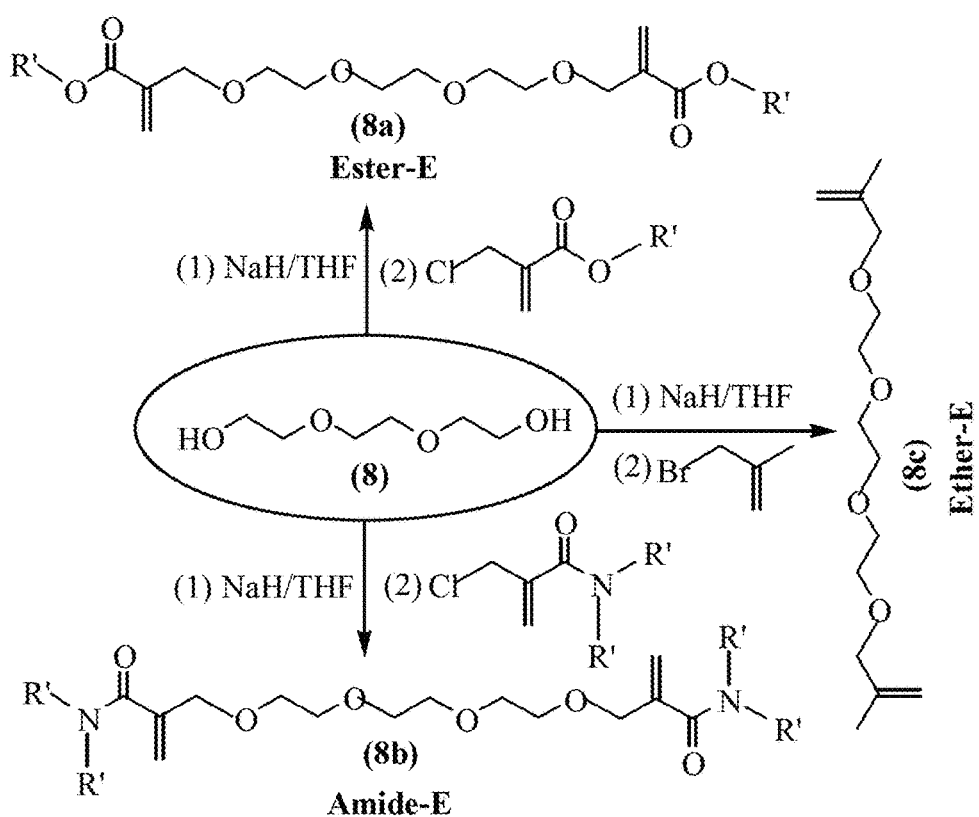
FIG. 6 illustrates one synthesis of flexible TEGDMA analogues: ether, ester and amide.

Strategy#3: synthesize ether-based monomer, such as shown in FIG. 5. Because ether is completely non-hydrolysable, the ether-based monomer is completely stable in the oral cavity and has no strength reduction with aging. In order to further reduce the shrinkage, the new monomers can be combined with rigid POSS (polyhedral oligomeric silsesquioxane) core (Strategy#5), thus the stiffness and strength can be improved, while the shrinkage will be reduced.

SYNTHESIZE LOW DEGRADABLE AMIDE BASED MONOMER—AMIDE A (3): Bisphenol-A (22.8 g) and NaOH (8.8 g) were added THF. Then, 2-chloroethylamine hydrochloride (29.0 g) was added and the solution was kept stirring at room temperature overnight. After being washed with saturated $NaHCO_3$ and water, the solvent was removed by a rotavap. Then, the crude product of amino bisphenol A (31.4 g), 2.2 g of TEA (triethylamine) and 0.3 g BHT (Butylated hydroxytoluene) was added into the flask. Under Ar protection, methacryloyl chloride (20.9 g) was added dropwise under ice bath. Alkylation of 3a was performed in DMSO at room temperature.

Figure 7:
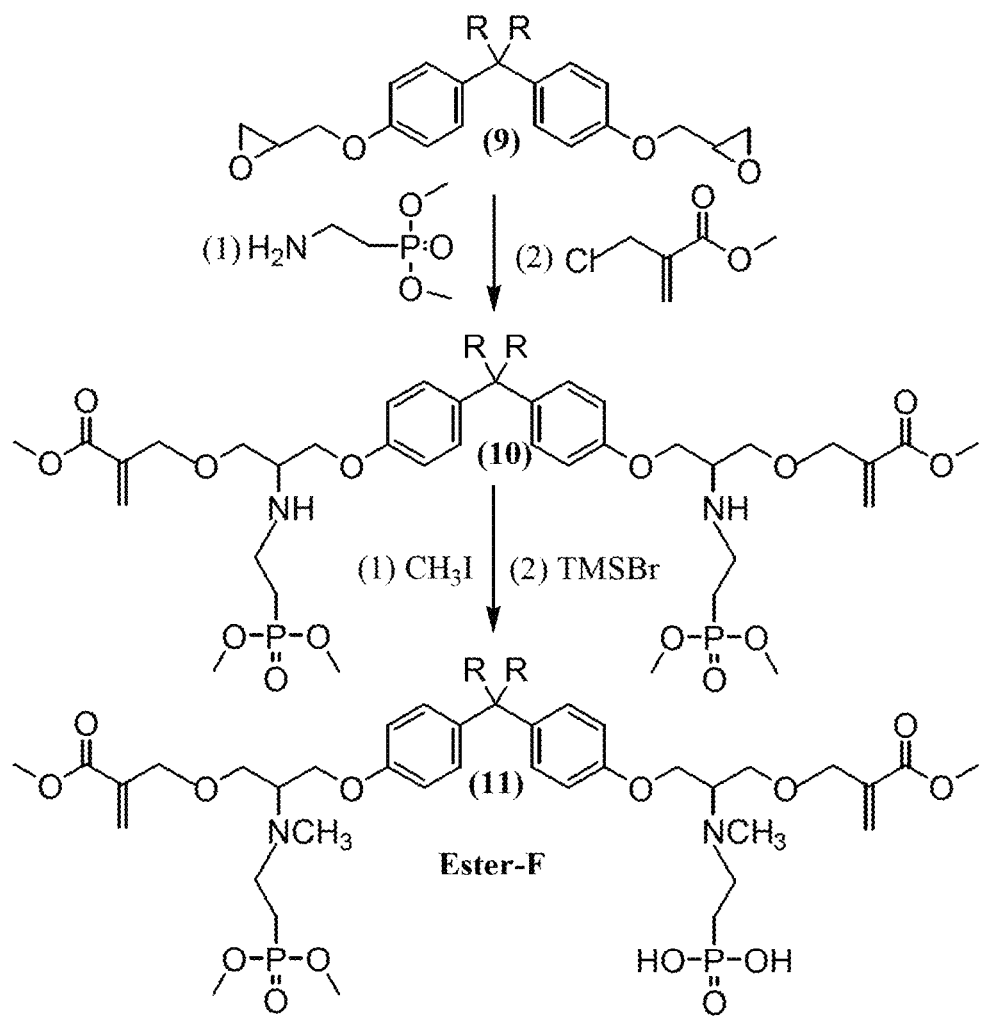
FIG. 7 illustrates one synthesis of hydrolytic stable resin containing phosphonic group.
Figure 8:
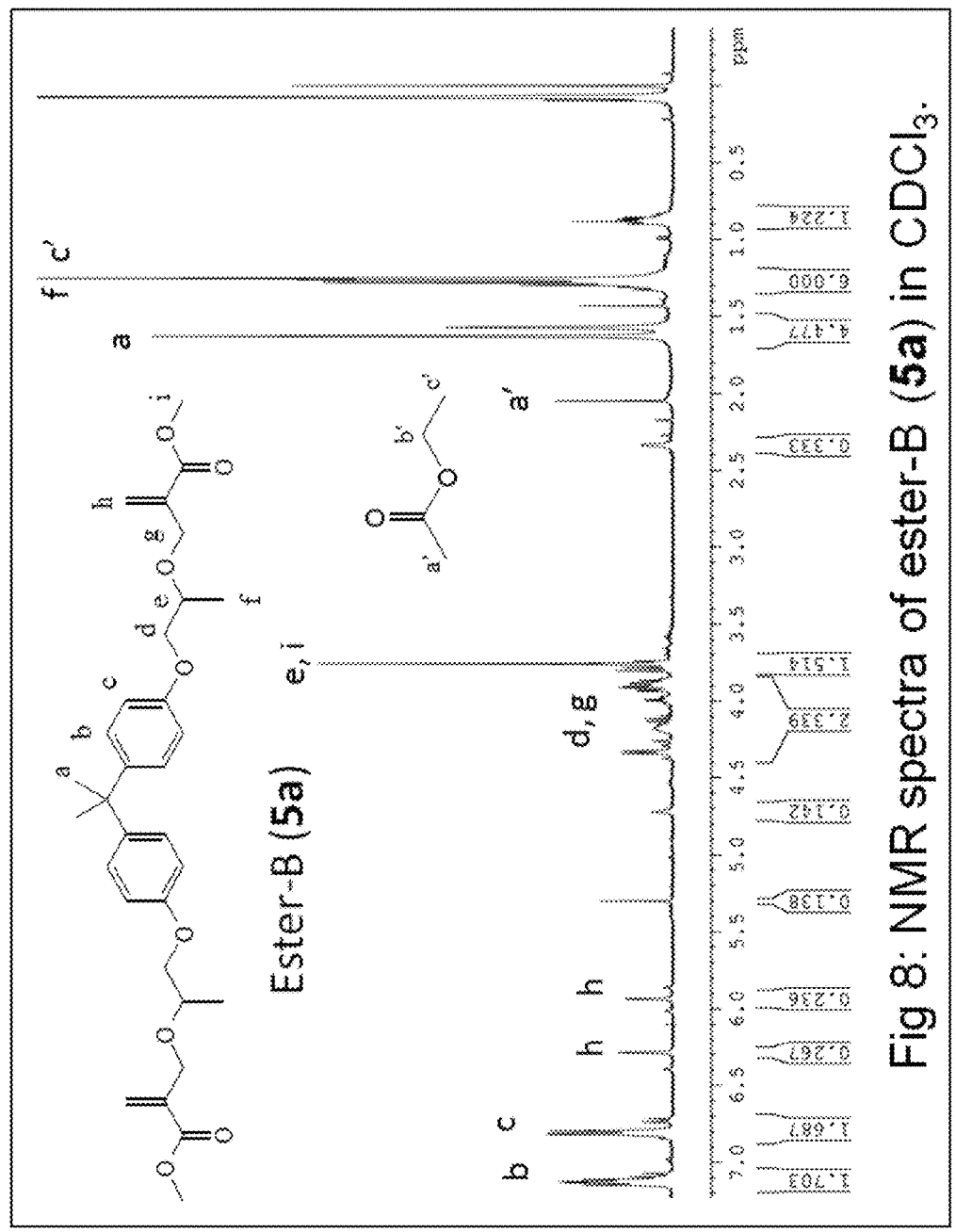
FIG. 8 illustrates one HNMR of the prepared monomer illustrated therein.

SYNTHESIZE MONOMERS WITH ESTER/AMIDE ON SIDE CHAINS OF POLYMERS: Propoxylated-bisphenol A (4) was synthesized via a direct nucleophilic ring-open of propylene oxide by bisphenol-A (FIG. 7). Bisphenol-A (57.0 g), and NaOH (20.0 g) were added into THF with Argon protection. After stirring at room temperature for 3 hours, propylene oxide (34.8 g) was added. After stirring overnight, the solution was acidified with 0.1 mol/L HCl and extracted with ethyl acetate, washed by water. After drying over anhydrous $Na_2SO_4$ overnight, the solvent was removed by a rotary evaporator.

Ester-B (5a) was synthesized according to modified procedures for (2) with NaH. 34.4 g of (4), NaH (5.3 g) and 0.3 g BHT were added into dry THF. After stirring for 2 hours, methyl 2-(chloromethyl)acrylate (33.6 g) were added under Ar protection. After stirring at room temperature overnight, the product was purified as that for (4). The crude product was further purified by silica gel column with ethyl acetate and methylene chloride (1/1v/v) as the eluant.

The formation of ester-B was confirmed by HPLC-MS. The chemical structure of ester-B was confirmed by $^1H$ NMR spectra, showing the characteristic chemical shifts at 7.1 ppm and 5.9 ppm, but with impurity of ethyl acetate (peaks a' and c').

SYNTHESIZE NON-DEGRADABLE MONOMER BASED ON ETHER BOND ABSENCE OF ESTER OR AMIDE: The ether based monomer (6) was synthesized via a one-step direct nucleophilic ring-open of allyl glycidyl ether on bisphenol-A (Ether-C). The synthesis was conducted according to that of (4) with the exception of using allyl glycidyl ether instead of propylene oxide.

Figure 11:
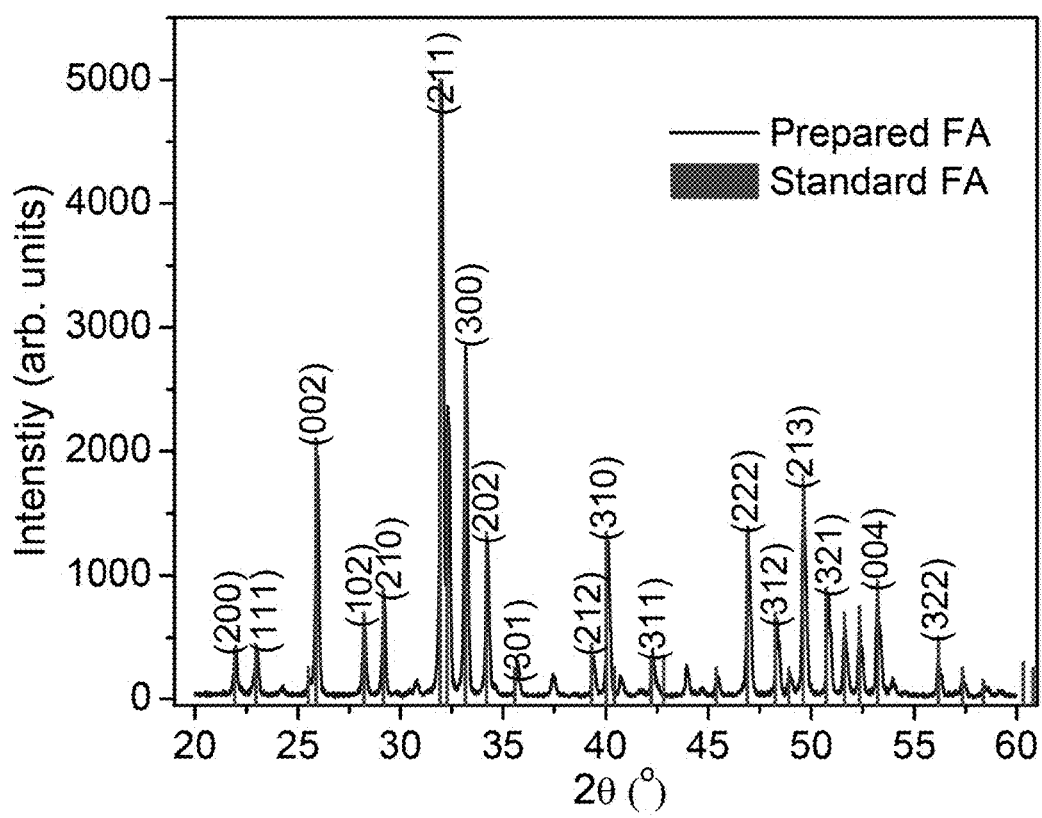
FIG. 11 illustrates an X-ray diffraction pattern of a prepared fluoroapatite (FA) filler.

One-step preparation of ether-C (6) provided satisfactory result of synthesis. While HPLC measurement confirmed the formation of ether-C, the chemical structure was confirmed by $^1H$ NMR spectra (FIG. 11), showing the existence of chemical shifts at 7.1 ppm and 5.9 ppm. By comparing the integration ratio of the above two peaks, the yield of allyl substitution is calculated about 65%, confirming that single-step reaction is favorable.

SYNTHESIZE MONOMER CONTAINING PHOSPHONIC ACID GROUP FOR ENHANCED BINDING WITH FA FILLER AND TOOTH: Synthesize Phosphonated Monomer (10 and 11): Phosphonated monomer was synthesized via a two step reaction. Bisphenol A diglycidyl ether (34.0 g) reacted with 38.3 g of aminoethylphosphonate dimethyl ester in dry THF under Ar at room temperature for 2 hours. Then, 25.3 g of TEA, 0.3 g of BHT, and 33.6 g of methyl 2-(chloromethyl)acrylate was added dropwise at room temperature and was kept overnight. Conversion from phosphonate ester (monomer 10) to phosphonic acid (ester-F, 11) was conducted according to Moszner's published method. (Moszner, N., Zeuner, F, Fischer, U. K., Rheinberger, V., "Monomers for Adhesive Polymers, 2. Synthesis and Radical Polymerisation of Hydrolytically Stable Acrylic Phosphonic Acids," *Macromolecular Chemistry and Physics*, 1999, 200: 1062-1067.)

PREPARE DENSE CERAMIC FA BY FURNACE: Dense ceramic FA powder was prepared according the chemical reaction: $3 \alpha\text{-}Ca_3(PO_4)_2 + CaF_2 \rightarrow 2 Ca_5(PO_4)_3F$. α-Tricalcium phosphate (α-TCP, $\alpha\text{-}Ca_3(PO_4)_2$) was prepared by heating 1 mol of calcium carbonate ($CaCO_3$) and 2 mol of calcium phosphate dibasic anhydrous (DCPA) in a furnace to 1200° C. for 6 hours and quenched in air. Calcium fluoride ($CaF_2$) was dried in an oven 105° C. for 3 hours. For stoichiometric FA with Ca:P:F molar ratio 5:3:1, 3 mol of α-TCP and 1 mol of $CaF_2$ was mixed and heated in a furnace 1500° C. for 6 hours to complete the conversion. By adjusting the proportion of the various calcium phosphate and calcium fluoride components in the mixture, a range of other dense calcium phosphate and calcium fluoride particles can be prepared.

XRD patterns from prepared FA is quantitatively similar to the standard FA JSPDS both in 2θ and intensity, particularly for the strong peaks at (002), (211), (300), (310), (222) and (213) (FIG. 12). (Chen, M. Jiang, D., Li, D., Zhu, J., Li, G., Xie, J., "Controllable Synthesis of Fluorapatite Nanocrystals with Various Morphologies: Effects of pH Value and Chelating Reagent," *Journal of Alloys and Compounds*, 2009, 485: 396-401.) No obvious peak from α-TCP and $CaF_2$ indicates the complete conversion into FA.

PREPARATION OF FA MICRO- AND NANO-PARTICLES BY BALL MILLING: FA microparticles were ground by a Retsch Planetary Ball Mill (Model PM400) for 24 hours at 200 rpm. The FA nanoparticles were ground at 1000 rpm by a Pulverisette 7 Premium Line machine.

Figure 9:
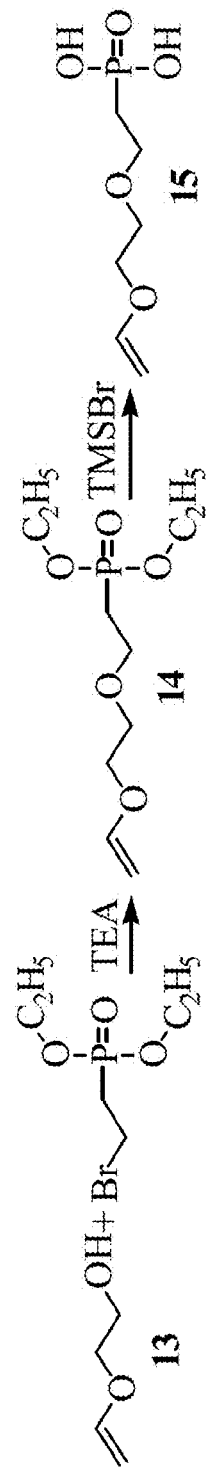
FIG. 9 illustrates one synthesis of new coupling agent for FA or calcium phosphate filler.
Figure 10:
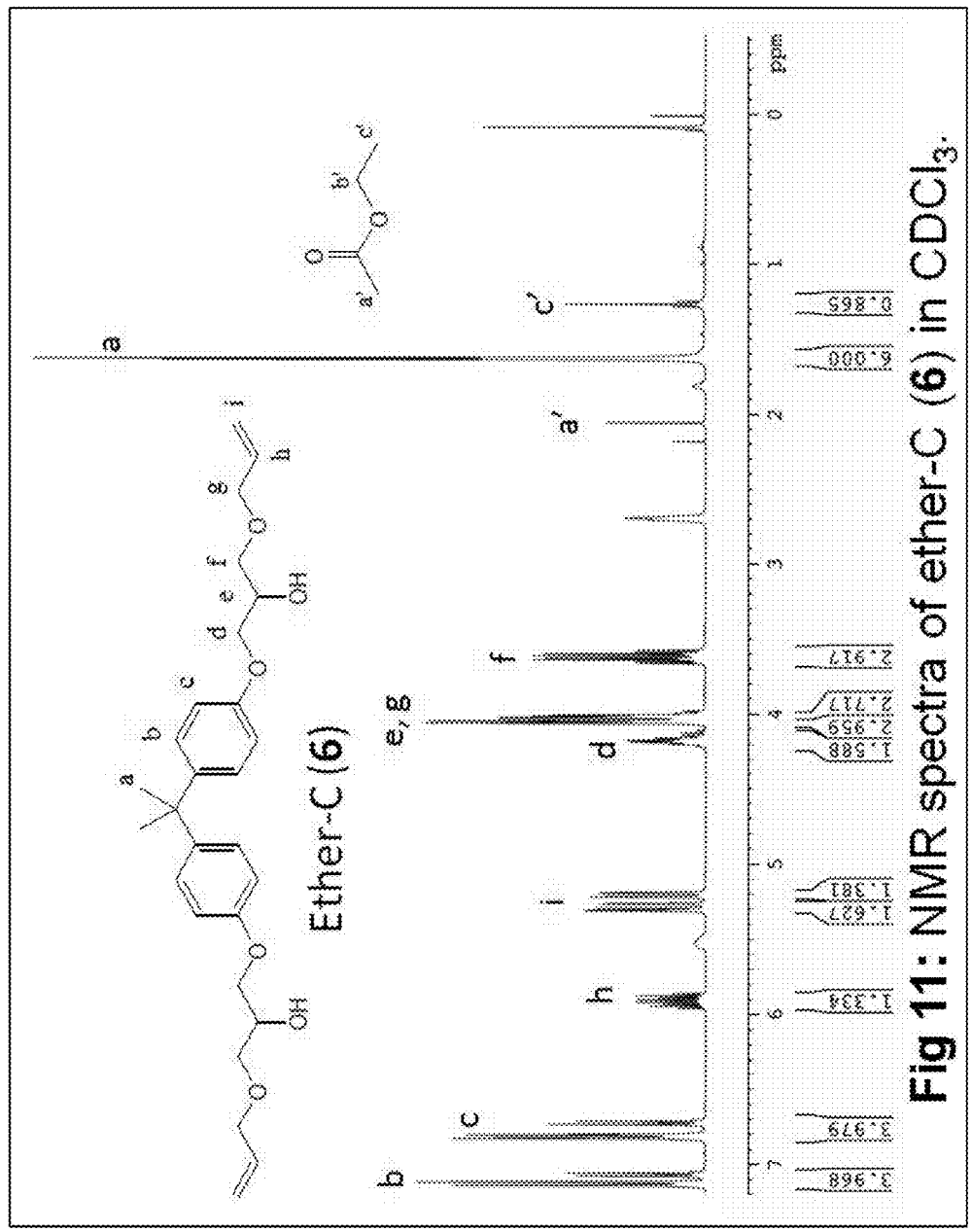
FIG. 10 illustrates one HNMR of the prepared monomer illustrated therein.

SYNTHESIZE HYDROLYTICALLY STABLE COUPLING AGENT: The new coupling agent vinyl glycidyl ethylphosphonic acid (FIG. 9) was synthesized according to the phosphorylation method for compound 10. This agent has a phosphonic group, which can strongly bind with FA and teeth. Only ether moieties instead of esters existing in the entire molecule make it hydrolytically stable.

COMBINE BALL MILLING AND SURFACE COATING: The phosphorus coupling agent was dissolved in ethanol to obtain concentrations relative to the filler in 1, 2, and 5% (w/w of coupling agent/filler). The fillers were coated by agitation or stirring for various times, preferably 2 hours, and were then separated using a centrifuge and washed by ethanol three times. The phosphorus coupling agent coated fillers were dried at room temperature under vacuum overnight.

In order to enhance the interfacial adhesion between resin matrix and FA particles and prevent agglomeration, we combined ball milling and coating with the coupling agent, thus the FA particle can be stabilized immediately during grinding, thus prevent the agglomeration In ball milling, the phosphorus coupling agent was added to the dispersion of filler in n-propanol which was dissolved in ethanol to obtain concentrations of 1, 2, and 5% (w/w). The fillers were coated by agitation or stirring for various times, preferably 2 hours, and were then separated using a centrifuge and washed by ethanol three times. The phosphorus coupling agent coated fillers were dried at room temperature under vacuum overnight.

COMPOSITES FABRICATION: The composite will be fabricated from the previously prepared hydrolytically stable monomers, densely ceramic FA filler, the initiator, and new phosphonic coupling agent coated FA particles. A monomer consisting of two monomers (one rigid and one flexible) at 1:1 mass ratio with 0.2% camphorquinone and 0.8% ethyl 4-N,N-dimethylaminobenzoate will be used for light-curable resin. Two types of FA, either nano-FA or micro-FA are milled as reinforcing materials at varied FA loading ratio. FA particles will be pre-mixed in varied mass ratio of micro-FA/nano-FA: 50:50%, 60:40%, 70:30%, and 80:20%. A monomer consisting of the same ratio of two monomers with 2% benzoyl peroxide, and 0.07% MEHQ will be used for heat curing. (Xu, H. H. K., "Long-Term Water-Aging of Whisker-Reinforced Polymer-Matrix Composites," *Journal of Dental Research*, 2003, 82(1): 48-52.) Heat-curing will be conducted in an oven (Model 48, Fisher Scientific) at 140° C. for 30 min to produce bar specimens. The paste mixed from fillers and monomer will be cured in a stainless steel mold (2×2×25 $mm^3$).

What is claimed is:

1. A dental composition comprising:
   a hydrolytically stable resin, the hydrolytically stable resin including a monomer lacking an ester or amide bond between a polymerizable double bond;
   a bioactive filler; and
   a coupling agent, the coupling agent lacking a hydrolysable ester bond, wherein the coupling agent has FA (fluoroapatite) or calcium phosphate binding groups, comprising phosphorus binding groups selected from the group consisting of phosphonic acid group ($—PO_3H_2$) as well as its salt and combinations and mixtures thereof.

2. The dental composition according to claim 1, wherein the bioactive filler includes at least one material selected from the group consisting of FA (fluorapatite), HA (hydroapatite), FHA (fluorhydroxyapatite), ACP (amorphous calcium phosphate), TCP (tricalcium phosphate), TTCP (tetracalcium phosphate), DCP (dicalcium phosphate), MCP (monocalcium phosphate), bioglass, quartz, glass, silicate, Ba/Sr/silicate glass, metal oxides, $YbF_3$, and mixtures thereof.

3. The dental composition of claim 1, wherein the filler can be used as major filler or minor filler.

4. The dental composition of claim 1, wherein the coupling agent includes a material selected from the group consisting of phosphorus group, carboxylic acid group, hydroxyl group, amino group, sulfonic acid group, as well as their salt, and combination and mixtures thereof.

5. A dental composition comprising:
   a hydrolytically stable resin, the hydrolytically stable resin including a monomer lacking an ester or amide bond between a polymerizable double bond;
   a bioactive filleri and
   a coupling agent, the coupling agent lacking a hydrolysable ester bond, wherein the coupling agent has the structure the general structure:

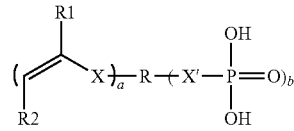

wherein the number of phosphonic groups and C=C double bonds independently can be 1, 2, 3, 4, 5, 6, 7, 8, 9, and/or 10, wherein R, R1 and/ or R2 are each independently selected from the group consisting of B, C, Si, O, S, N, P, H, $(CH2)_p$, $(CF2)_q$, $(CHF)_q$, C=O, C=C, C≡C, benzyl, phenyl, F, Cl, Br, I, $NO_2$ and any combination thereof, where p and q are independently 0, 1, 2, 3, 4, 5, 6, 7, 8, 9, 10, 11, 12, 13, 14, 15, 16, 17, 18, 19, or 20;

wherein X, and/or X' are each independently selected from the group consisting of B, C, Si, O, S, N, P, H, $(CH2)_p$, $(CF2)_q$, $(CHF)_q$, C=O, C=C, C≡C, benzyl, phenyl, F, Cl, Br, I, $NO_2$;

wherein the number of a and b can each independently be 1, 2, 3, 4, 5, 6, 7, 8, 9, and/ or 10;

wherein the phosphorus group can be replaced by carboxylic, sulfonic, hydroxyl or amine group.

6. The dental composition of claim 1, wherein the filler can be coated after preparation of filler or with preferable method to combine surface coating and ball milling into one single step.

7. The dental composition of claim 1, wherein the monomer has greater water resistance than BisGMA and TEGDMA.

8. The dental composition of claim 1, wherein the monomer has the general structure:

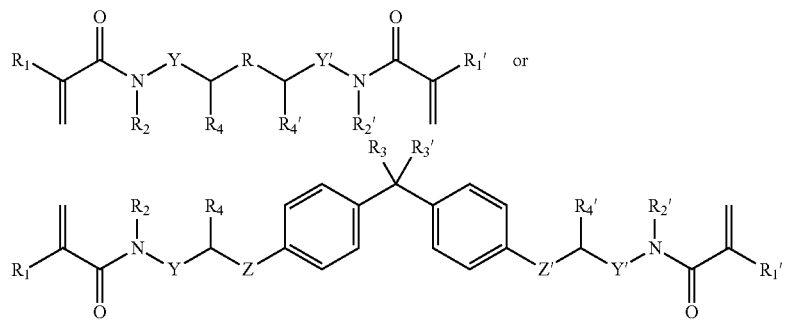

or wherein R is selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$ or any combination thereof, where p and q can each independently be 0, 1, 2, 3, 4, 5, 6, 7, 8, 9, 10, 11, 12, 13, 14, 15, 16, 17, 18, 19, or 20;

wherein Y, Z, Y' and/ or Z' are each independently selected from the group consisting of B, C, Si, O, S, N, P, H, (CH2)p, (CF2)q, (CHF)q, C=O, C=C, C≡C, benzyl, phenyl, F, Cl, Br, I, $NO_2$ or any combination thereof, or combination with any of —OH, —COOH, —$PO_3H_2$, where p and q can each independently be 0, 1, 2, 3, 4, 5, 6, 7, 8, 9, 10, 11, 12, 13, 14, 15, 16, 17, 18, 19, or 20;

wherein R1, R1', R2, and/or R2' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$, —COOH, —$PO_3H_2$ or any combination thereof, where p and q can each independently be 0, 1, 2, 3, 4, 5, 6, 7, 8, 9, 10, 11, 12, 13, 14, 15, 16, 17, 18, 19, or 20; and wherein R3, R4, R3', and/or R4' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$, —COOH, —$PO_3H_2$ or any combination thereof, where p and q can each independently be 0, 1, 2, 3, 4, 5, 6, 7, 8, 9, 10, 11, 12, 13, 14, 15, 16, 17, 18, 19, or 20.

9. The dental composition of claim 1, wherein the monomer has the general structure:

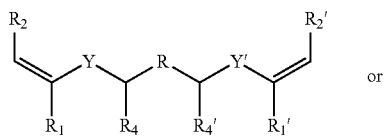

or

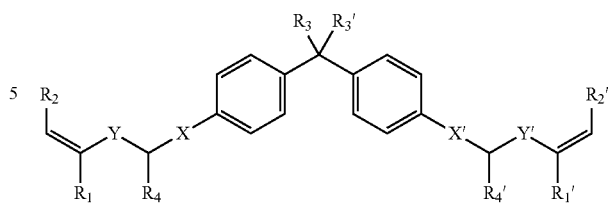

wherein R is selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$ and any combination thereof, where p and q can each independently be 0, 1, 2, 3, 4, 5, 6, 7, 8, 9, 10, 11, 12, 13, 14, 15, 16, 17, 18, 19, or 20;

wherein X, Y, X' and/or Y' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$ and any combination thereof, where p and q can each independently be 0, 1, 2, 3, 4, 5, 6, 7, 8, 9, 10, 11, 12, 13, 14, 15, 16, 17, 18, 19, or 20;

wherein R1, R1', R2, and/or R2' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$, —COOH, —$PO_3H_2$ and any combination thereof, where p and q can each independently be 0, 1, 2, 3, 4, 5, 6, 7, 8, 9, 10, 11, 12, 13, 14, 15, 16, 17, 18, 19, or 20; and wherein R3, R4, R3', and/or R4' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$, —COOH, —$PO_3H_2$ and any combination thereof, where p and q can each independently be 0, 1, 2, 3, 4, 5, 6, 7, 8, 9, 10, 11, 12, 13, 14, 15, 16, 17, 18, 19, or 20.

10. The dental composition of claim 1, wherein the monomer has the general structure:

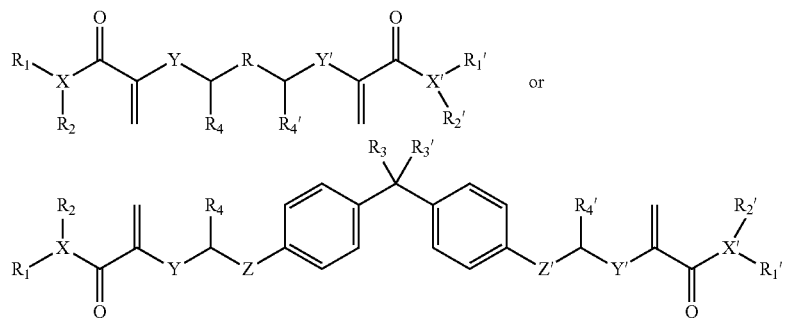

wherein R is selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$ or any combination thereof, where p and q can each independently be 0, 1, 2, 3, 4, 5, 6, 7, 8, 9, 10, 11, 12, 13, 14, 15, 16, 17, 18, 19, or 20;

wherein X, Y, Z, X', Y', and/or Z' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$ or any combination thereof, where p and q can each independently be 0, 1, 2, 3, 4, 5, 6, 7, 8, 9, 10, 11, 12, 13, 14, 15, 16, 17, 18, 19, or 20;

wherein $R_1$, R1', R2, and/or R2' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$, —COOH, —$PO_3H_2$ or any combination thereof, where p and q can each independently be 0, 1, 2, 3, 4, 5, 6, 7, 8, 9, 10, 11, 12, 13, 14, 15, 16, 17, 18, 19, or 20; and wherein R3, R4, R3', and/or R4' are each independently selected from the group consisting of B, C, Si, O, S, N, P, H, $(CH_2)_p$, $(CF_2)_q$, $(CHF)_q$, C=O, C=C, C≡C, benzyl, phenyl, F, Cl, Br, I, $NO_2$, —COOH, —$PO_3H_2$ or any combination thereof, where p and q can each independently be 0, 1, 2, 3, 4, 5, 6, 7, 8, 9, 10, 11, 12, 13, 14, 15, 16, 17, 18, 19, or 20.

11. The dental composition of claim 1, wherein the monomer includes a calcium binding group selected from the group consisting of phosphonic, phosphoryl, carboxylic, sulfonic, hydroxyl, amino, as well as their salt, and combination or mixtures thereof.

12. The dental composition of claim 1, wherein the hydrolytically stable resin is effective to resist hydrolysis.

13. The dental composition of claim 1, wherein the bioactive filler has similar chemical composition with tooth, including calcium, or phosphate, or fluoride or combination and mixtures thereof, thus the calcium and phosphate in saliva can remineralize on the filler or composite.

14. The dental composition of claim 1, wherein the coupling agent includes a polymerizable double bond and a calcium binding group selected from the group consisting of a phosphorus group, a carboxylic acid, an amino group, a hydroxyl group, a sulfonic group, and/or their salt form.

15. The dental com-position of claim 1, A dental composition comprising:
a hydrolytically stable resin, the hydrolytically stable resin including a monomer lacking an ester or amide bond between a polymerizable double bond;
a bioactive filler; and
a coupling agent the coupling agent lacking a hydrolysable ester bond, wherein the coupling agent has the structure the general structure:

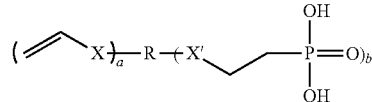

wherein R is selected from the group consisting of O, S, N, H, $(CH_2)_p$, $(CF_2)_q$, or any combination thereof, where p and q are independently 0, 1, 2, 3, 4, 5, 6, 7, 8, 9, 10, 11, 12, 13, 14, 15, 16, 17, 18, 19, or 20;

wherein X and X' are independently selected from the group consisting of $CH_2$, O, S, or N; where the number of a orb can independently be 1, 2, 3, 4, 5, 6, 7, 8, 9, 10;

wherein the phosphorous group can be replaced by carboxylic, sulfonic, hydroxyl or amine groups; wherein the number of phosphonic group and C=C double bonds can be 1, 2, 3, 4, 5, 6, 7, 8, 9, 10.

UNITED STATES PATENT AND TRADEMARK OFFICE
CERTIFICATE OF CORRECTION

PATENT NO. : 10,485,735 B2
APPLICATION NO. : 14/895771
DATED : November 26, 2019
INVENTOR(S) : Tongxin Wang et al.

It is certified that error appears in the above-identified patent and that said Letters Patent is hereby corrected as shown below:

In the Specification

At Column 1, after Line 12, please insert --GOVERNMENT INTEREST
GOVERNMENT LICENSE RIGHTS (1) This invention was made with government support under contract number R01 DE021786 awarded by the National Institute of Health. The government has certain rights in the invention.--

Signed and Sealed this
Eighth Day of November, 2022

Katherine Kelly Vidal
*Director of the United States Patent and Trademark Office*